United States Patent [19]

Pieniak

[11] Patent Number: 4,488,923
[45] Date of Patent: Dec. 18, 1984

[54] METHOD FOR PRODUCING A FABRIC HAVING UNSECURED ELASTIC IN AREAS INTERMITTENTLY DISPOSED ALONG AN EDGE THEREOF

[75] Inventor: Heinz A. Pieniak, North Brunswick, N.J.

[73] Assignee: Personal Products Company, Milltown, N.J.

[21] Appl. No.: 570,332

[22] Filed: Jan. 13, 1984

Related U.S. Application Data

[63] Continuation-in-part of Ser. No. 325,611, Nov. 27, 1981, abandoned.

[51] Int. Cl.³ .............................................. B32B 31/08
[52] U.S. Cl. .................................. 156/199; 112/121.26; 156/229; 156/269; 156/292; 156/324; 156/495
[58] Field of Search ............. 156/204, 205, 229, 164, 156/292, 210, 163, 265, 495, 199, 324, 269; 604/385; 112/121.26

[56] References Cited

U.S. PATENT DOCUMENTS

| | | | |
|---|---|---|---|
| 1,184,748 | 5/1916 | Hicks | 156/205 |
| 2,480,316 | 8/1949 | Blair et al. | 156/205 |
| 3,804,688 | 4/1974 | Hillenbrand et al. | 156/470 |
| 3,860,003 | 1/1975 | Buell | 604/285 |
| 4,081,301 | 3/1978 | Buell | 156/291 |
| 4,227,952 | 10/1980 | Sabee | 156/204 |
| 4,285,747 | 8/1981 | Rega | 156/164 |
| 4,324,245 | 4/1982 | Mesek et al. | 604/385 |
| 4,331,501 | 5/1982 | Teed | 604/385 |
| 4,333,782 | 6/1982 | Pieniak | 156/229 |
| 4,337,771 | 7/1982 | Pieniak et al. | 604/385 |
| 4,379,016 | 4/1983 | Stemmler | 156/164 |
| 4,397,704 | 8/1983 | Frick | 156/265 |
| 4,417,938 | 11/1983 | Sigl | 156/164 |
| 4,425,173 | 1/1984 | Frick | 156/164 |
| 4,437,860 | 3/1984 | Sigl et al. | 604/385 |

*Primary Examiner*—Jerome Massie
*Attorney, Agent, or Firm*—Martha A. Michaels

[57] ABSTRACT

This invention comprises pleating a fabric, securing an elastic member in a relaxed state to the pleated fabric and then removing the pleats from the fabric. On removing the pleats, the elastic member is stretched to provide elastic areas in the previously pleated portions and non-elastic areas in the previously unpleated portions of the fabric.

9 Claims, 4 Drawing Figures

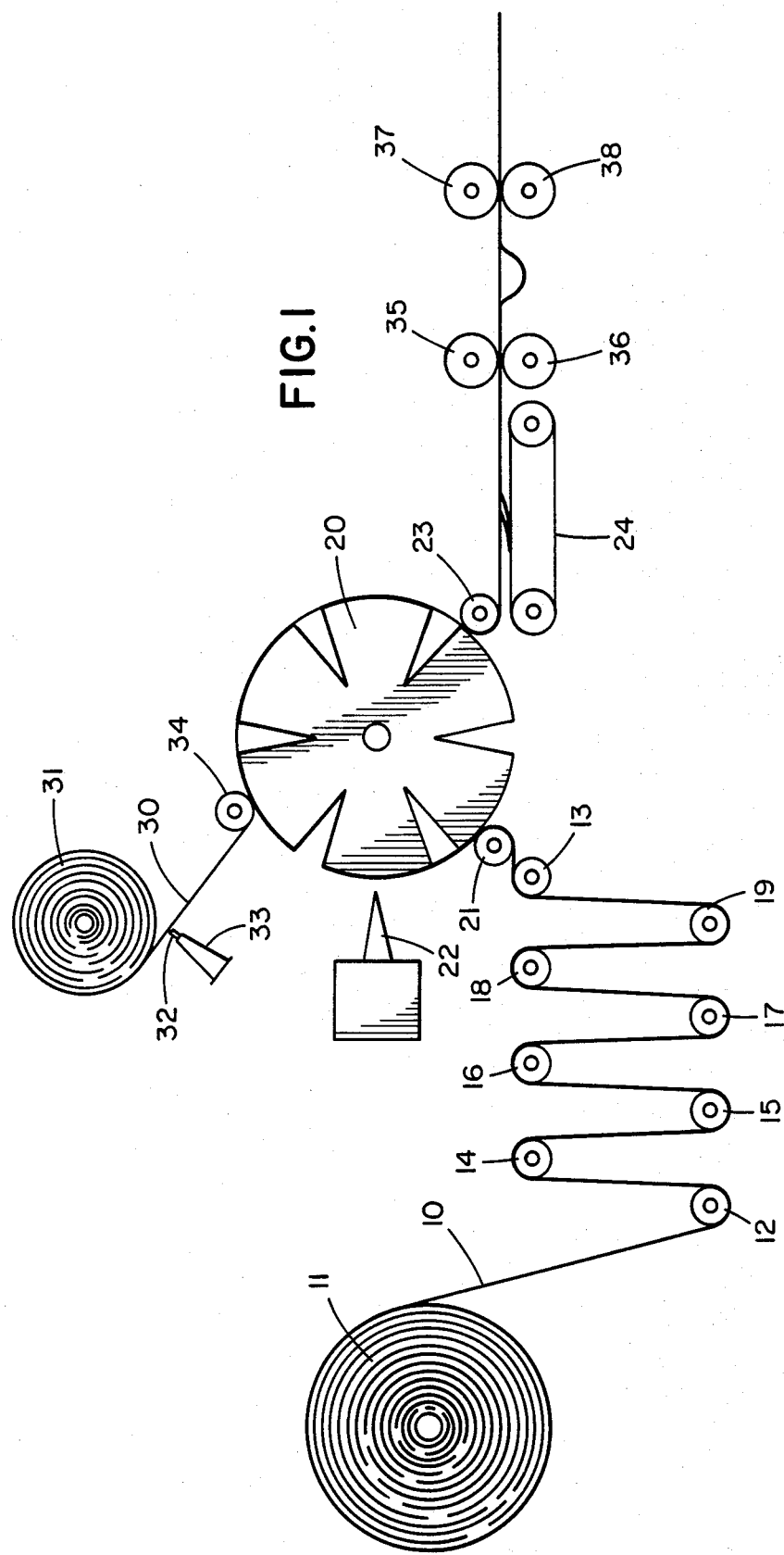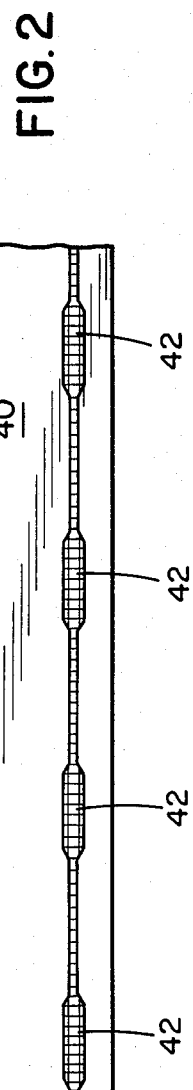

METHOD FOR PRODUCING A FABRIC HAVING UNSECURED ELASTIC IN AREAS INTERMITTENTLY DISPOSED ALONG AN EDGE THEREOF

This is a continuation-in-part of copending application Ser. No. 325,611, filed Nov. 27, 1981, now abandoned.

BACKGROUND OF THE INVENTION

Disposable Diapers have met with increased commercial acceptance in recent years, primarily because of their convenience as opposed to cloth diapers which need to be laundered when once soiled. Many different constructions have been proposed and some have met with widespread commercial acceptance in spite of certain inadequacies in commercial properties.

Also, in recent years, disposable diapers having elastic or leg-encircling portions have also entered the market, and even though being more costly to produce and more expensive to the consumer, still have gained acceptance in the disposable diaper market.

Examples of such stretch or elastic disposable diapers are described in U.S. Pat. Nos. 3,860,003 and 4,050,462. Also, in U.S. Pat. No. 4,801,301 there is shown one method and apparatus for making disposable diapers that have elasticized or stretchable leg-encircling portions. Furthermore, in a recently issued U.S. Pat. No. 4,227,952, there is shown yet another method and apparatus for making diapers with elastic bands in them.

The economics in the manufacture of disposable diapers is extremely important and disposable diapers must be made at fast rates of speed with low cost materials and in the most efficient manner with the least amount of waste in order to produce a product that is accepted in the marketplace from the price standpoint. In view of this, it becomes very important to develop methods and apparatus for accomplishing these purposes, and the simpler and more reliable the method and apparatus, the more economical will be the manufacturing operations.

In the manufacture of stretchable or elasticized disposable diapers, one of the most important parameters is to produce diapers that consistently have the same amount of stretch or elasticity in their leg-encircling portions and also to produce individual diapers that have the same elasticity or stretchability in both of their leg-encircling portions.

SUMMARY OF THE PRESENT INVENTION

The present invention represents a specific and improved technique over previous techniques for manufacturing stretchable or elasticized disposable diapers. In the new method and apparatus, one is able to produce diapers that substantially always have the same amount of stretching force or elastic force in the opposed leg-encircling portions. Furthermore, the new method produces diapers that consistently have the same amount of stretch in both their leg-encircling portions. The new method produces these disposable diapers at high rates of speed and with considerably accuracy, reliability and reproducibility to reduce the waste produced in the disposable diaper manufacturing operation.

In accordance with the present invention, the fabric is moved along a first path. Spaced apart or intermittent sections of the fabric are moved out of that first path and then substantially returned to the first path to produce pleats and foreshorten the longitudinal length of the fabric. An elastic member in a substantially relaxed state is secured along the longitudinal edge of the fabric while the fabric is in the foreshortened condition. The pleats are removed from the fabric by stretching the fabric; i.e., returning it to its previously unforshortened condition. This step stretches the elastic member in the areas where it is not secured to the fabric; i.e., the pleated areas. Subsequent securement of the stretched elastic to the fabric is not necessary and preferably, is omitted. The stretched areas produce the elasticized or leg-encircling portions in a diaper when the fabric is combined with other layers to produce disposable diapers as is well known in the manufacture of disposable diapers.

Further objects, advantages and features of this invention will become apparent from the disclosure.

DESCRIPTION OF THE DRAWINGS

FIG. 1 is a diagrammatic side elevational view of one form of apparatus for performing the method of the present invention;

FIG. 2 is a plan view of a web having elastic and inelastic portions produced in accordance with the method of the present invention;

DETAILED DESCRIPTION OF THE DRAWINGS

Figure 3:
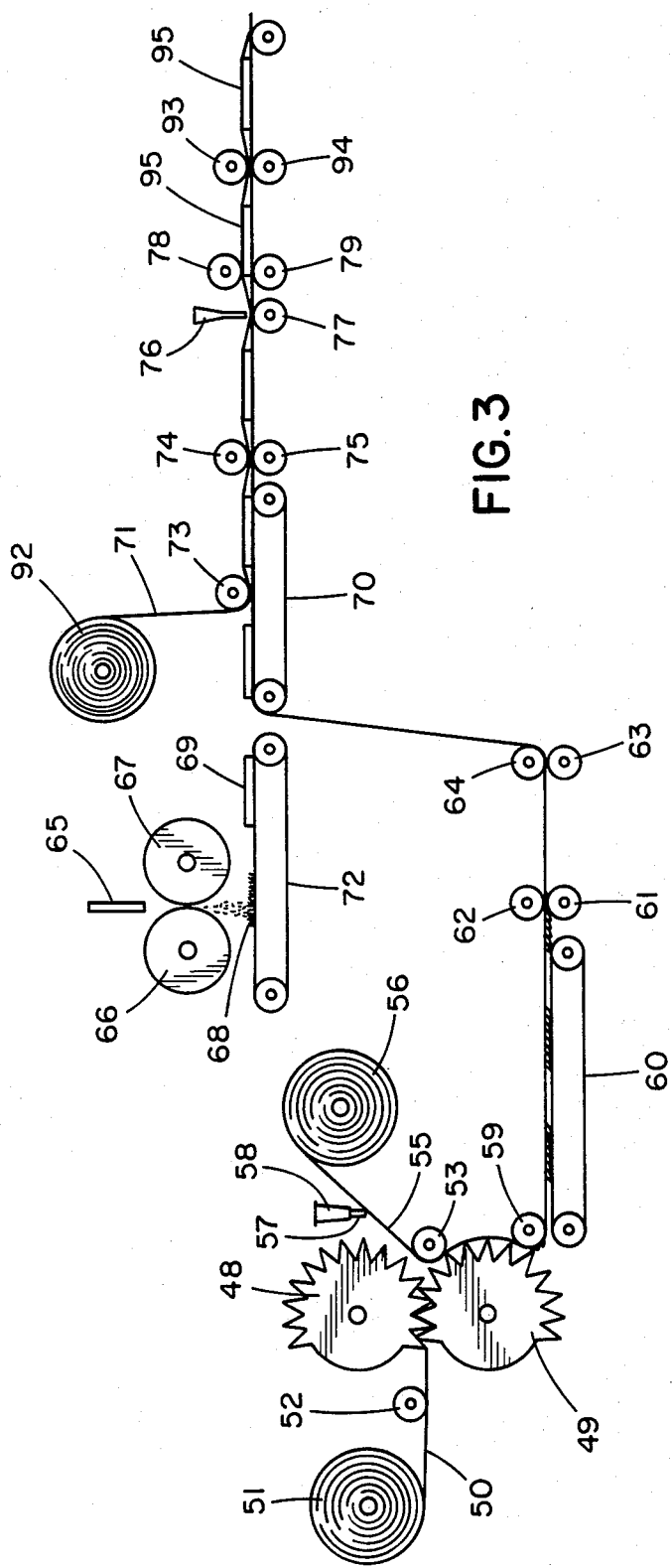
FIG. 3 is a diagrammatic side elevational view of another form of apparatus for producing disposable diapers in accordance with the method of the present invention.

Referring to FIG. 1, a substantially inelastic web 10 is fed from a supply roll 11 to a plurality of dancer rolls. The dancer rolls comprise a first and a last stabilizing roll 12 and 13 with a plurality of rolls 14, 15, 16, 17, 18 and 19 positioned therebetween that can move on their axis up and down in the vertical direction. Dancer rolls are well known in the art and are used to intermittently feed material at varying rates of speed. The rolls are mounted to allow them to converge towards one another when more material has to be fed; i.e., the material is fed at a faster rate of speed. The rolls are urged away from one another when it is desired to slow down the rate of feed of the material. In this apparatus, material is fed through the group of dancer rolls, past a guide roll 21 to a rotatable roll 20. An arm 22 extends and forces the fabric 10 out of the plane of its normal path into the crevices of the rotatable roll 20. The length of the fabric displaced into the crevice represents the length of the crotch region in the diaper to be produced. The distance on the rotatable roll 20 between the crevices represents the distance from one crotch region in a diaper to the crotch region of a second diaper when the diapers are laid end to end. An elastic member 30 is fed from a suitable supply roll 31 to the surface of the roll 20 which surface is covered by fabric 10. Adhesive 32 is applied to the surface of the elastic member 30 by a nozzle 33. In the alternative, the adhesive may be applied to the web and the elastic member secured thereto. The elastic member 30 in an unstretched state is pressed against the surface of the web by roll 34 and adhered to the web on the surface of the rotatable roll. As the fabric elastic-member laminate leaves the roll, the fabric tucked in the crevice of the roll is in the form of a pleat. The laminate is guided past roll 23 onto a conveyor 24. The web with the elastic member adhered thereon is then passed through two pairs of nip rolls. The first pair of nip rolls 35 and 36 rotate at a peripheral linear speed equal to the speed of the pleated web and the second pair of nip rolls 37 and 38 rotate at a faster peripheral linear speed to remove the pleats from the web and stretch the elastic member in the area that had contained the pleat.

As shown in FIG. 2, the resulting web 40, when returned to its fully extended condition, has intermittent stretched elastic areas 41, which may be used to gather the web in that area, combined with areas of unstretched elastic 42 or areas where the web is not gathered. In order to make a fabric which has uniform gathered or gatherable areas and ungathered or ungatherable areas, it is usually desirous to place the elastic members adjacent the longitudinal edges of the web.

Once a material is made as described above, it is then a simple matter to combine this material having gatherable and ungatherable areas with a plurality of absorbent pads and impervious backing sheet or another web member by standard laminating techniques. The laminate is severed between pads to produce a plurality of disposable diapers or other disposable products.

Referring to FIG. 3 of the drawings, there is shown a schematic representation of apparatus for producing a multiplicity of individual disposable diapers utilizing the method of the present invention. In this embodiment, an impervious backing material 50, preferably a polyolefin film material, is fed from a suitable supply roll 51 by roll 52 to the nip of special rolls 48 and 49. The special rolls are provided with meshing teeth which provide a series of small pleats in the material. A pair of elastic members 55 are supplied from suitable supply rolls 56. Adhesive 57 is applied to one surface of the elastic members by nozzles 58 as the members are fed so as to contact the backing material disposed on the top of the raised areas. The elastic member as applied is in a substantially relaxed state and once applied to the top of the raised members, a suitable compression roll 59 presses the elastic with the adhesive on its surface against the inelastic backing to adhere the elastic member thereto. The material elastic-member laminate containing a multiplicity of pleats in the material is conveyed on conveyor 60 to the nip of rolls 61 and 62. The rolls 61 and 62 rotate at a peripheral linear speed equal to the speed of the pleated material. The laminate is then fed to the nip of a set of rolls 63 and 64 rotating at a faster peripheral linear speed to remove the pleats from the material and stretch the elastic member in the area that had contained the pleats.

Pulp board 65 is ground by a pair of rotating toothed rolls 66 and 67 to produce a pulp fluff 68 which is deposited on a conveyor 72 in intermittently spaced apart panels 69 of the wood pulp fluff. The inelastic web with the elastic adhered thereto is conveyed by conveyor 70 adjacent the absorbent panels and the absorbent panels of wood pulp fluff disposed on the backing in spaced apart positions. A second inelastic web 71, in this embodiment a facing web, from supply roll 92 is guided by roller 73 to the top of the absorbent panels and is adhered to the backing web along the marginal edges of the panel and between absorbent panels by suitable compression rolls 74 and 75, as is well known in the manufacture of disposable diapers. A suitable cutting knife 76 working in cooperation with an anvil roll 77 severs the laminate between absorbent panels to produce a plurality of disposable diapers. The diapers 95 are separated by two sets of rolls 78 and 79, and 93 and 94 rotating at different peripheral linear speeds.

Figure 4:
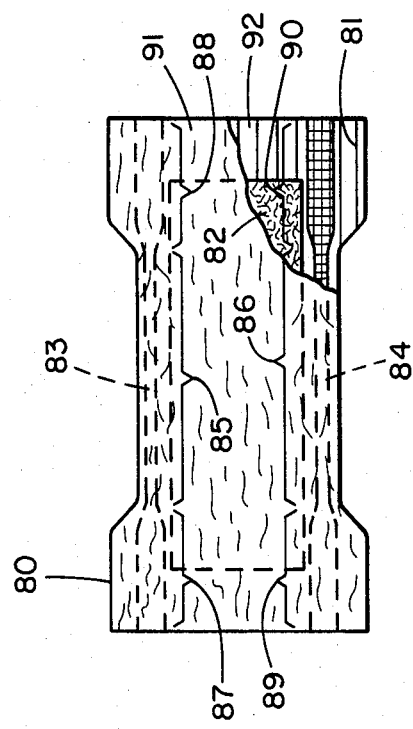
FIG. 4 is a plan view of a disposable diaper produced in accordance with the method of the present invention.

Referring to FIG. 4 there is shown an enlarged plan view of a disposable diaper 80 made by the method and apparatus described in accordance with FIG. 3. The diaper comprises a backing layer 81 of a polyolefin film or similar impervious film. Disposed inwardly from the longitudinal edges and the transverse edges of the film is an absorbent panel 82 comprising wood pulp fibers. Disposed along the longitudinal edges of this panel and adhered to the impervious backing film are a pair of elastic members 83 and 84. The elastic members are stretched in the center portions 85 and 86 but are unstretched or relaxed at the end portions 87, 88, 89, and 90. A suitable facing material 91, co-extensive with the backing material, is disposed on the top of the batt and is adhered to the backing along their longitudinal and transverse edges by adhesive lines 92 to produce a disposable diaper.

In an alternate method to that shown in FIG. 3, the facing or second web may also be pleated and combined with the backing or first web and the elastic prior to returning both webs to their original length. It is also contemplated that the elastic may be secured to either or both webs as they are combined and in the method of producing disposable diapers, the absorbent pad is fed between the combining webs.

It should be noted that although I have described only adhesive securement of the elastic member, the elastic members may be secured by any conventional means, such as heat sealing, sonic sealing, etc.

It should be also pointed out that although I have described the present invention with regard to a disposable diaper, it could, of course, be used in the manufacture of various other articles. Also, it should be noted that the elastic members could be applied to a fabric and that fabric rolled up and then the fabric, at some later time, combined with other materials to form a plurality of individual products having elasticized and non-elasticized areas. Furthermore, although I have described with regard to FIGS. 3 and 4, the application of the elastic members to the impervious backing member of the disposable diaper, it should be clear that the elastic members could be applied to the facing fabric of disposable diapers as well and then combined with the absorbent pad and an impervious backing member.

What is claimed is:

1. A method for producing a plurality of individual disposable diapers, each diaper having elasticized legband portions disposed between opposing waistband portions comprising:
(a) feeding a web of substantially inelastic material along a first path;
(b) intermittently foreshortening said web by moving said web out of the plane of said first path and then returning it to the plane of the first path;
(c) securing an elastic member in a substantially relaxed condition along each longitudinal edge of said web that is in the plane of said first path while said web is in the foreshortened condition;
(d) returning said web to its original length in said first path whereby the elastic members between adjacent secured areas are stretched and unsecured;
(e) disposing a plurality of spaced absorbent panels on said web, the central portion of said panels being adjacent stretched portions of the elastic members and the space between the panels being in the area where the elastic members are secured;

(f) securing a second continuous substantially inelastic web to said first substantially inelastic web along substantially the entire longitudinal edge of said webs; said (g) severing said combined webs in the areas between adjacent panels to produce a plurality of individual disposable diapers.

2. A method according to claim 1 wherein one of the inelastic webs is an impervious polyolefin film.

3. A method according to claim 1 wherein the elastic members are secured to the web by applying adhesive to a surface of the elastic members and then urging that adhesive surface into contact with the web.

4. A method according to claim 1 or 3 wherein the second inelastic web is combined with the first inelastic web by a plurality of adhesive lines placed on the surface of the first inelastic web that contacts said second inelastic web.

5. A method of producing a laminate having elasticized areas uniformly intermittently disposed along a longitudinal edge portion of said laminate comprising:

(a) moving a first layer of said laminate along a first path;

(b) intermittently moving said first layer out of the plane of said first path and substantially immediately returning it to the plane of said first path in a position adjacent to the position from which it had been removed to form a pleat and foreshorten the longitudinal length of said first layer;

(c)
  (i) moving a second layer of said laminate along a second path;
  (ii) intermittently moving said second layer out of the plane of said second path and substantially immediately returning it to the plane of said second path in a position adjacent to the position from which it had been removed to form a pleat and foreshorten the longitudinal length of said second layer;

(d) combine said second layer with said first layer so that the pleats of the first and second layers coincide;

(e) securing an elastic member in a substantially relaxed state along the longitudinal edge of said first layer and/or said second layer while said layer(s) is in the foreshortend condition, said member being secured to the portions of said layer(s) lying in the plane of said first path; and (f) removing the foreshortened portions from said laminate by moving the laminate in its entirety to the plane of said first path whereby the elastic member is stretched in the areas where it is not secured to a layer.

6. The method of claim 5 wherein step (e) is carried out before step (c).

7. A method for producing a plurality of individual disposable diapers, each diaper having elasticized legband portions disposed between opposing waistband portions comprising:

(a) feeding a web of substantially inelastic material along a first path;

(b) intermittently forshortening said web by moving said web out of the plane of said first path and then returning it to the plane of the first path;

(c)
  (i) moving a second continuous substantially inelastic web along a second path;
  (ii) intermittently moving said second web out of the plane of said second path and substantially immediately returning it to the plane of said second path in a position adjacent to the position from which it has been removed to form a pleat and foreshorten the longitudinal length of said second layer;

(d) combining said second continuous substantially inelastic web with said first substantially inelastic web along the longitudinal edges such that the pleats coincide; and (e) disposing a plurality of spaced absorbent panels between said webs, the central portion of said panels being adjacent the pleats in said webs;

(f) securing an elastic member in a substantially relaxed condition along each longitudinal edge of either or both of said webs that are in the plane of said first path while said web is in the foreshortened condition;

(g) returning said web to its original length in said first path whereby the elastic members between adjacent secured areas are stretched and unsecured; and (h) severing said combined webs in the areas between adjacent panels to produce a plurality of individual disposable diapers.

8. The method of claim 7 wherein step (f) is carried out before step (d).

9. The method according to claim 7 or 8 wherein the second inelastic web is combined with the first inelastic web by a plurality of adhesive lines placed on the surface of the first inelastic web that contacts said second inelastic web.

* * * * *